US012734118B2

(12) United States Patent
Arora et al.

(10) Patent No.: US 12,734,118 B2
(45) Date of Patent: Sep. 15, 2026

(54) ORAL CARE COMPOSITIONS

(71) Applicant: Colgate-Palmolive Company, New York, NY (US)

(72) Inventors: Payal Arora, Bridgewater, NJ (US); Harsh Mahendra Trivedi, Hillsborough, NJ (US); James Masters, Ringoes, NJ (US); Rabab Ahmed, Somerset, NJ (US); Sarita Vera Mello, North Brunswick, NJ (US); Sergio Leite, Monmouth Junction, NJ (US)

(73) Assignee: Colgate-Palmolive Company, New York, NY (US)

( * ) Notice: Subject to any disclaimer, the term of this patent is extended or adjusted under 35 U.S.C. 154(b) by 723 days.

(21) Appl. No.: 17/250,582

(22) PCT Filed: Nov. 12, 2020

(86) PCT No.: PCT/US2020/070772

§ 371 (c)(1),
(2) Date: Feb. 5, 2021

(87) PCT Pub. No.: WO2021/097483

PCT Pub. Date: May 20, 2021

(65) Prior Publication Data

US 2022/0304907 A1 Sep. 29, 2022

Related U.S. Application Data

(60) Provisional application No. 62/936,157, filed on Nov. 15, 2019.

(51) Int. Cl.

| | |
|---|---|
| ***A61K 8/34*** | (2006.01) |
| ***A61K 8/36*** | (2006.01) |
| ***A61Q 11/00*** | (2006.01) |

(52) U.S. Cl.
CPC .................. *A61K 8/34* (2013.01); *A61K 8/36* (2013.01); *A61Q 11/00* (2013.01)

(58) Field of Classification Search
CPC .............................. A61K 31/192; A61K 31/19
USPC ............................................ 514/167; 424/49
IPC ................................ A61K 31/19; A61Q 11/00
See application file for complete search history.

(56) References Cited

U.S. PATENT DOCUMENTS

| | | | |
|---|---|---|---|
| 5,004,597 A | 4/1991 | Majeti et al. | |
| 5,952,317 A | 9/1999 | Deluca et al. | |
| 9,078,864 B2 | 7/2015 | Gudmundsson et al. | |
| 9,682,026 B2 | 6/2017 | Kohli et al. | |
| 9,877,929 B2 | 1/2018 | Brown et al. | |
| 9,889,089 B2 | 2/2018 | Golden | |
| 2005/0281758 A1 | 12/2005 | Dodd et al. | |
| 2006/0246016 A1* | 11/2006 | Burzynski | A61K 8/4926 424/49 |
| 2009/0202450 A1 | 8/2009 | Prencipe et al. | |
| 2009/0292455 A1 | 11/2009 | Abendroth et al. | |
| 2010/0273748 A1 | 10/2010 | Gallo et al. | |
| 2010/0297197 A1 | 11/2010 | Golden | |
| 2010/0317734 A1 | 12/2010 | Folan et al. | |
| 2011/0118217 A1* | 5/2011 | Gudmundsson | A61P 1/00 514/557 |
| 2012/0213714 A1 | 8/2012 | Huang et al. | |
| 2017/0281538 A1* | 10/2017 | Golden | A61K 9/0053 |
| 2018/0110729 A1 | 4/2018 | Golden | |
| 2018/0161292 A1* | 6/2018 | Kuang | A23L 33/40 |
| 2019/0076343 A1 | 3/2019 | Curatola | |
| 2019/0125636 A1 | 5/2019 | Prencipe et al. | |

FOREIGN PATENT DOCUMENTS

| | | | |
|---|---|---|---|
| CN | 101889969 | 11/2010 | |
| CN | 101925346 | 12/2010 | |
| CN | 101959429 A | 1/2011 | |
| CN | 104853715 | 8/2015 | |
| CN | 104968351 A | 10/2015 | |
| WO | WO-0010958 A1 * | 3/2000 | C07C 37/20 |
| WO | 2014/059143 | 4/2014 | |
| WO | 2014/100930 | 7/2014 | |
| WO | 2021/097483 | 5/2021 | |
| WO | 2021/097484 | 5/2021 | |

OTHER PUBLICATIONS

Dietrich et. al., 2005, "Association between serum concentrations of 25-hydroxyvitamin D and gingival Inflammation," Am. J. Clin. Nutr.82(3):575-580.

Garcia et al., 2011, "One-year effects of vitamin D and calcium supplementation on chronic periodontitis," Journal of Periodontology 82(1):25-32.

Hewison, 2010, "Vitamin D and the intracrinology of innate immunity," Molec. Cellular Endocrinology 321(2):103-111.

Nizet et al., 2003, "Cathelicidins and innate defense against invasive bacterial infection," Scand. J. Infect. Dis. 35(9):670-676.

Grant et al., 2008, "Vitamin-D, periodontal disease, tooth loss, and cancer risk", The Lancet Oncology, Elsevier, 9(7):612-613.

Hangzhou Jiaojie, 2015, "Strawberry Flavoured Toothpaste for Children", Mintel Database GNPD AN: 3667771.

International Search Report and the Written Opinion of the International Searching Authority issued in International Application PCT/US2020/070772 mailed Feb. 23, 2021.

International Search Report and the Written Opinion of the International Searching Authority issued in International Application PCT/US2020/070773 mailed Feb. 25, 2021.

Mcmahon et al., 2011, "Vitamin D-Mediated Induction of Innate Immunity in Gingival Epithelial Cells", Infection and Immunity, 79(6):2250-2256.

Namel Nanometer Technology, 2019, "Strawberry Flavoured Toothpaste for Children", Mintel Database GNPD AN: 6921657.

(Continued)

*Primary Examiner* — Walter E Webb

(57) ABSTRACT

Described herein are oral care compositions comprising vitamin D, or a derivative thereof; an alkanoic acid of formula R—COOH or an alkali metal salt thereof, wherein R is a $C_1$ to $C_{13}$ hydrocarbyl group; and an orally acceptable carrier. Methods of making and using same are also described.

16 Claims, 3 Drawing Sheets

(56) References Cited

OTHER PUBLICATIONS

Schauber J et al., 2003, "Expression of the cathelicidin LL-37 is modulated by short chain fatty acid in colonocytes: Relevance of signalling pathways", Gut Microbiota, British Medical Association 52(5):735-741.
Denish et al., "Discovery of a natural cyan blue: A unique food-sourced anthocyanin could replace synthetic brilliant blue," Science Advances, vol. 7, No. 15, pp. 1-8, Apr. 7, 2021.
Menzel, et al., 2019, "Activation of Vitamin D in the gingival epithelium and its role in gingival inflammation and alveolar bone loss", J Periodontal Res., vol. 54(4), 444.
Nylén et al., "Boosting innate immunity: Development and validation of a cell-based screening assay to identify LL-37 2 inducers," Innate Immunity, vol. 20, Iss. 4, pp. 364-376, Year: 2014.
Van der Does et al., 2012, "Induction of the human cathelicidin LL-37 as a novel treatment against bacterial infections", Journal of Leukocyte Biology, 92, 735.

* cited by examiner

PBA = Phenylbutyric Acid

ORAL CARE COMPOSITIONS

BACKGROUND

Periodontal disease results from initial colonization by keystone pathogens, such as *Porphyromonas gingivalis*, which leads to a bacterial dysbiosis, and inflammatory response. This inflammation ultimately leads to bone loss and tooth loss that is characteristic of periodontal disease. Epidemiological studies have indicated an association between vitamin D deficiency and both chronic and aggressive periodontitis. This may be due to the recently identified relationship between vitamin D and the expression of innate immune mediators and pro-inflammatory cytokines.

Development and validation of a cell-based screening assay to identify LL-37 inducers was described by F. Nylén et al. in *Innate Immunity* 2014, vol. 20, iss. 4, pp 364-376. Innate immunity, the front line of our defense against pathogens, relies, to a great extent, on the production of antimicrobial peptides (AMPs). These peptides exhibit antimicrobial activity and immunomodulatory properties. In humans, AMPS include the defensins (α- and β-families) and the cathelicidin, LL-37. Bacterial resistance against antibiotics is a growing concern, and novel antimicrobial strategies are needed urgently. Hence, the concept of strengthening immune defenses against infectious microbes by inducing AMP expression may represent novel or complementary pharmaceutical interventions in the treatment or prevention of infections. A robust cell-based reporter assay for LL-37 expression, which serves as a marker for a healthy epithelial barrier, was developed and validated. Such reporter assay can be a powerful tool for high-throughput screenings.

Topical vitamin D and ubiquinol oral supplement compositions is disclosed in U.S. Pat. No. 9,877,929. A topical vitamin D and UBIQUINOL supplement composition useful in treating oral inflammation and reducing oxidative stress comprising: a supplement mixture of vitamin D and UBIQUINOL in an aqueous-free emulsion containing: spilanthes extract, stabilizing compositions for UBIQUINOL and trans-oral mucosal absorption facilitators for the supplement mixture; where the emulsion forms a mucoadhesive gel in the presence of saliva, that effects passive diffusion through the oral mucosa of the supplement mixture and spilanthes extract regulating: in vivo availability and immune response of the supplement mixture, and maintaining adequate levels of circulating vitamin D and of adjunctively administered UBIQUINOL, while minimizing the risk of hypercalcemia.

Dietary supplement non-fluoride toothpaste and methods of making and using the same have been disclosed in U.S. Patent Application Publication No. 20180110729. Provided therein was a storage stable non-fluoride toothpaste composition enriched with a dietary supplement containing both oil soluble and water soluble vitamins. The dietary supplement was incorporated into the toothpaste, the dietary supplement containing a water-soluble vitamin portion including at least one water-soluble vitamin and an oil-soluble vitamin portion. The oil soluble vitamin portion included at least one oil-soluble vitamin, carrier oil, and an emulsifier. The toothpaste was thereby formulated in a manner such that oral application will result in systemic delivery of at least a portion of the dietary supplement to meet a 2% RDI threshold even when 3 or less serving sizes are orally applied.

Oral care formulations comprising vitamin D is disclosed in U.S. Patent Application Publication No. 20190076343. The publication discloses an oral care product comprising at least one of phytomenadione (vitamin $K_1$), menaquinone (vitamin $K_2$), vitamin C, selenium, ubiquinone (Coenzyme $Q_{10}$), Astragalus, Ginseng, Schisandra, adaptogenic herbs, cannabidiol, or the like. An oral care product directed toward rebalancing micro-bacterial homeostasis in the mouth, or establishing and maintaining a healthy oral microbiome are disclosed.

Vitamin D and the intracrinology of innate immunity has been discussed in M. Hewison, *Molec. Cellular Endocrinology,* 2010, vol. 321, iss. 2, pp. 103-111. An immunomodulatory role for vitamin D was first proposed prior to 1985, based on two salient observations. Firstly it was shown that monocytes/macrophages from patients with the granulomatous disease, sarcoidosis, constitutively synthesize the active form of vitamin D, 1,25-dihydroxyvitamin D ($1,25(OH)_2D$) from precursor 25-hydroxyvitamin D (250 HD). Secondly, the receptor for $1,25(OH)_2D$ (vitamin D receptor, VDR) is detectable in activated, proliferating lymphocytes. These observations suggested a mechanism whereby 1,25(OH).sub.2D produced by monocytes could act upon adjacent T-cells or B-cells, but the impact of such a system on normal immune system regulation was uncertain. Indeed, it is only in recent years that a much clearer picture of the role of vitamin D as a determinant of immune responsiveness has emerged. Two concepts have prompted this change. Firstly, studies of innate immunity have shown that intracrine induction of antimicrobial activity by vitamin D is a pivotal component of monocyte/macrophage response to infection. Secondly, it is now clear that sub-optimal vitamin D status is a common feature of many populations throughout the world, with the potential to compromise monocyte/macrophage metabolism of 250 HD and subsequent actions of $1,25(OH)_2D$. The publication reviewed the details of these new developments with specific reference to the metabolic and signaling mechanisms associated with innate immune regulation by vitamin D and implications for human disease.

Association between serum concentrations of 25-hydroxyvitamin D and gingival inflammation has been proposed in T. Dietrich et. al., *Am. J. Clin. Nutr.* 2005, vol. 82, iss. 3, pp 575-580. Data from 77,503 gingival units (teeth) in 6,700 never smokers aged 13 to >90 y from the third National Health and Nutrition Examination Survey has been analyzed. Multiple logistic regression models adjusted for subject- and site-specific covariates included age, sex, race-ethnicity, income, body mass index, diabetes, use of oral contraceptives and hormone replacement therapy among women, intake of vitamin C, missing teeth, full crown coverage, presence of calculus, frequency of dental visits, and dental examiner and survey phase. Generalized estimating equations were used to account for correlated observations within subjects. Compared with sites in subjects in the lowest 25(OH)D quintile, sites in subjects in the highest 25(OH)D quintile were 20% (95% CI: 8%, 31%) less likely to bleed on gingival probing (P for trend<0.001). The association appeared to be linear over the entire 25(OH)D range, was consistent across racial or ethnic groups, and was similar among men and women as well as among users and nonusers of vitamin and mineral supplements. It has been concluded that vitamin D may reduce susceptibility to gingival inflammation through its anti-inflammatory effects and that gingivitis may be a useful clinical model to evaluate the anti-inflammatory effects of vitamin D.

One-year effects of vitamin D and calcium supplementation on chronic periodontitis has been disclosed in M. N. Garcia et al., *Journal of Periodontology,* 2011, vol. 82, No. 1, pp. 25-32. Fifty-one patients enrolled in maintenance programs from two dental clinics were recruited. Of these, 23 were taking vitamin D (≥400 IU/day) and calcium (≥1,000 mg/day) supplementation, and 28 were not. All subjects had at least two interproximal sites with ≥3 mm clinical attachment loss. For mandibular-posterior teeth, gingival index, plaque index, probing depth, attachment loss, bleeding on probing, calculus index, and furcation involvement were evaluated. Photostimulable-phosphor, posterior bitewing radiographs were taken to assess alveolar bone. Daily vitamin D and calcium intakes were estimated by nutritional analysis. Data were collected at baseline, 6 months, and 12 months. Total daily calcium and vitamin D intakes were 1,769 mg (95% confidence interval, 1,606 to 1,933) and 1,049 IU (781 to 1,317) in the taker group, and 642 mg (505 to 779) and 156 IU (117 to 195) in the non-taker group, respectively ($P<0.001$ for both). Clinical parameters of periodontal health improved with time in both groups ($P<0.001$). When clinical measures were considered collectively, the differences between supplement takers and non-takers had the following P values: baseline ($P=0.061$); 6 months ($P=0.049$); and 12 months ($P=0.114$). After adjusting for covariates, the P values for the effect of supplementation were as follows: baseline ($P=0.028$); 6 months ($P=0.034$); and 12 months ($P=0.058$). Calcium and vitamin D supplementation (<1,000 IU/day) had a modest positive effect on periodontal health, and consistent dental care improved clinical parameters of periodontal disease regardless of such supplements. Our findings support the possibility that vitamin D may positively impact periodontal health and confirm the need for randomized clinical trials on the effects of vitamin D on periodontitis.

Cathelicidins and innate defense against invasive bacterial infection were discussed by V. Nizet and R. L. Gallo in *Scand. J. Infect. Dis.* 2003, vol. 35, iss. 9, pp. 670-676. Cathelicidins are small cationic peptides that possess broad-spectrum antimicrobial activity. These gene-encoded 'natural antibiotics' are produced by several mammalian species on epithelial surfaces and within the granules of phagocytic cells. Since their discovery over a decade ago, cathelicidins have been speculated to function within the innate immune system, contributing to the first line of host defense against an array of microorganisms. Consequently, cathelicidins have captured the interest of basic investigators in the diverse fields of cell biology, immunology, protein chemistry and microbiology. A burgeoning body of experimental research now appears to confirm and extend the biological significance of these fascinating molecules. This article reviews the latest advances in the knowledge of cathelicidin antimicrobial peptides, with particular emphasis on their role in defense against invasive bacterial infection and associations with human disease conditions.

Calcitriol derivatives and their uses are disclosed in U.S. Pat. No. 5,952,317. Calcitriol can be regulated to thus provide controlled release of vitamin D in vivo over time, by changing or modifying the hydrolyzable groups. Structurally, the key feature of the modified vitamin D compounds having desirable biological attributes is that they are derivatives of 25-dihydroxyvitamin D3, or derivatives of 25-dihydroxyvitamin D analogs, in which a hydrolysable group is attached to the hydroxyl group of carbon 25 and, optionally, to any other of the hydroxyl groups present in the molecule. Depending on various structural factors, e.g. the type, size, structural complexity of the attached group, these derivatives are thought to hydrolyze to 25-dihydroxyvitamin D3, or to a 25-dihydroxyvitamin D3 analog, at different rates in vivo, thus providing for slow release of the biologically active vitamin D compound (i.e. 1,25-dihydroxyvitamin D3, or an analog thereof) in the body. The slow release in vivo activity profiles of such compounds can be further modulated by the use of mixtures of derivatives (e.g. mixtures of different derivatives of 1,25-dihydroxyvitamin D3, or different derivatives of 1,25-dihydroxyvitamin D analogs) or the use of mixtures consisting of one or more vitamin D derivatives together with chemically modified molecules derived from $1,25(OH)_2D3$. Modifications have been made throughout the molecule to obtain analogs with the desired properties.

The use of 1,25-dihydroxyvitamin D3 analogs as immunomodulatory agents has been discussed by C. Mathieu and L. Adorini in Trends in Molecular Medicine. The active form of vitamin D, 1,25-dihydroxyvitamin D3 (i.e., $1,25(OH)_2D3$), is a secosteroid hormone that regulates calcium and bone metabolism, controls cell proliferation and differentiation, and exerts immunoregulatory activities. This range of functions has been exploited clinically to treat a variety of conditions, from secondary hyperparathyroidism to osteoporosis, to autoimmune diseases such as psoriasis. Recent advances in understanding $1,25(OH)_2D3$ functions and novel insights into the mechanisms of its immunomodulatory properties suggest wider applicability of this hormone in the treatment of autoimmune diseases and allograft rejection.

Although many advances in the art of formulating oral care composition have been made with respect to improving its ability to treat diseases, many more challenges remain.

BRIEF SUMMARY

The present invention is directed to an oral care composition comprising: vitamin D, or a derivative thereof.

Certain embodiments of the present invention may further comprise a humectant (e.g. sorbitol). In some embodiments, the sorbitol is in the form of a sorbitol solution. Sorbitol solution is a liquid aqueous humectant vehicle comprising sorbitol. In some embodiments, the sorbitol solution is a sorbitol syrup. In some embodiments, the sorbitol solution comprises about 30 wt % to about 80 wt % of the oral care composition.

Sorbitol is a sugar alcohol with a sweet taste which the human body metabolizes slowly. Sorbitol may be obtained by reduction of glucose, which changes the aldehyde group to a hydroxyl group.

In some embodiments, compositions of the present invention comprise an abrasive. In some embodiments, the abrasive comprises a silica. The silica particle may be prepared by any means known or to be developed in the art, and may be surface modified, if desired, to increase the capacity of the particle to adhere to a tooth surface. Under one embodiment, the silica comprises precipitated silica. Precipitated silica is an amorphous form of silica (silicon dioxide, $SiO_2$), which is a white, powdery material. Under one embodiment, the silica comprises fumed silica.

Examples of silica include ZEODENT® silica, SYLODENT® silica, Tixosil® silica, SORBOSIL silica.

In some embodiments, the compositions of the present invention comprise thickening silica. In some embodiments, the weight ratio of the thickening silica to the abrasive silica is between 1:4 to 1:0.25.

Under one embodiment, the vitamin D is selected from the group consisting of: vitamin D1, ergocalciferol, lumisterol, vitamin D2, vitamin D3, cholecalciferol, vitamin D4, 22-dihydroergocalciferol, vitamin D5, sitocalciferol, calcitriol, vitamin D compounds with hydroxyl groups at 1, 3 and 25 carbon positions, esters of 1α,25-dihydroxy vitamin D3, esters of 1,25-dihydroxy vitamin D3, 1,25 $(OH)_2D3$ analogs of $1,25(OH)_2D3$, 25(OH)D3, analogs of 25(OH)D3 and mixtures thereof. In certain embodiments, the vitamin D is cholecalciferol.

Vitamin D3 is cholecalciferol, also known as colecalciferol. Cholecalciferol is a type of vitamin D which is made by the skin when exposed to sunlight; it is also found in some foods and can be taken as a dietary supplement. Cholecalciferol is used to treat diseases associated with vitamin D deficiency, familial hypophosphatemia, hypoparathyroidism that is causing low blood calcium, and Fanconi syndrome.

Cholecalciferol is made in the skin following UV-B (about 280-315 nm) light exposure. Cholecalciferol is converted in the liver to calcifediol, i.e., 25-hydroxyvitamin D, which is then converted in the kidney to calcitriol, i.e., 1,25-dihydroxyvitamin D. One of the actions of cholecalciferol is to increase the uptake of calcium by the intestines.

The present invention provides an oral care composition which may be used to prevent a pathological condition by boosting host tissue antimicrobial peptides (AMPs) in oral cavity. Antimicrobial peptides, also called host defense peptides, play an important part of the innate immune response found among all classes of life. Such peptides may be potent, broad-spectrum antibiotics which demonstrate potential as novel therapeutic agents.

The present invention is also directed to a method of boosting host tissue antimicrobial peptide in the oral cavity by applying toothpaste to a portion of the oral cavity.

The data demonstrate that topical application of active form of vitamin D ($1,25(OH)_2D3$) to of gingival epithelial cells (GEC) induces enhanced expression of anti-microbial peptide (LL-37) proteins and thus helps in maintaining innate defense in oral gingival cells. The data shows that GEC are capable of converting the inactive forms to the active form as well. Therefore, it is hypothesized that topical application of vitamin D, both inactive and active, directly to the GEC, can lead to an overall therapeutic effect on the etiology and development of periodontal disease.

In some embodiments, the oral care composition further comprises a toothpaste ingredient selected from: a surfactant, a desensitizing agent, a hydrophilic polymer, a tartar control agent, a binder, a thickening agents, a detergent, an adhesion agents, a foam modulator, a pH modifying agent, a mouthfeel agent, a sweetener, a flavorant, a coloring agent, a humectant, a fluoride source, a viscosity modifier, and a mixture thereof.

DETAILED DESCRIPTION

Figure 1:
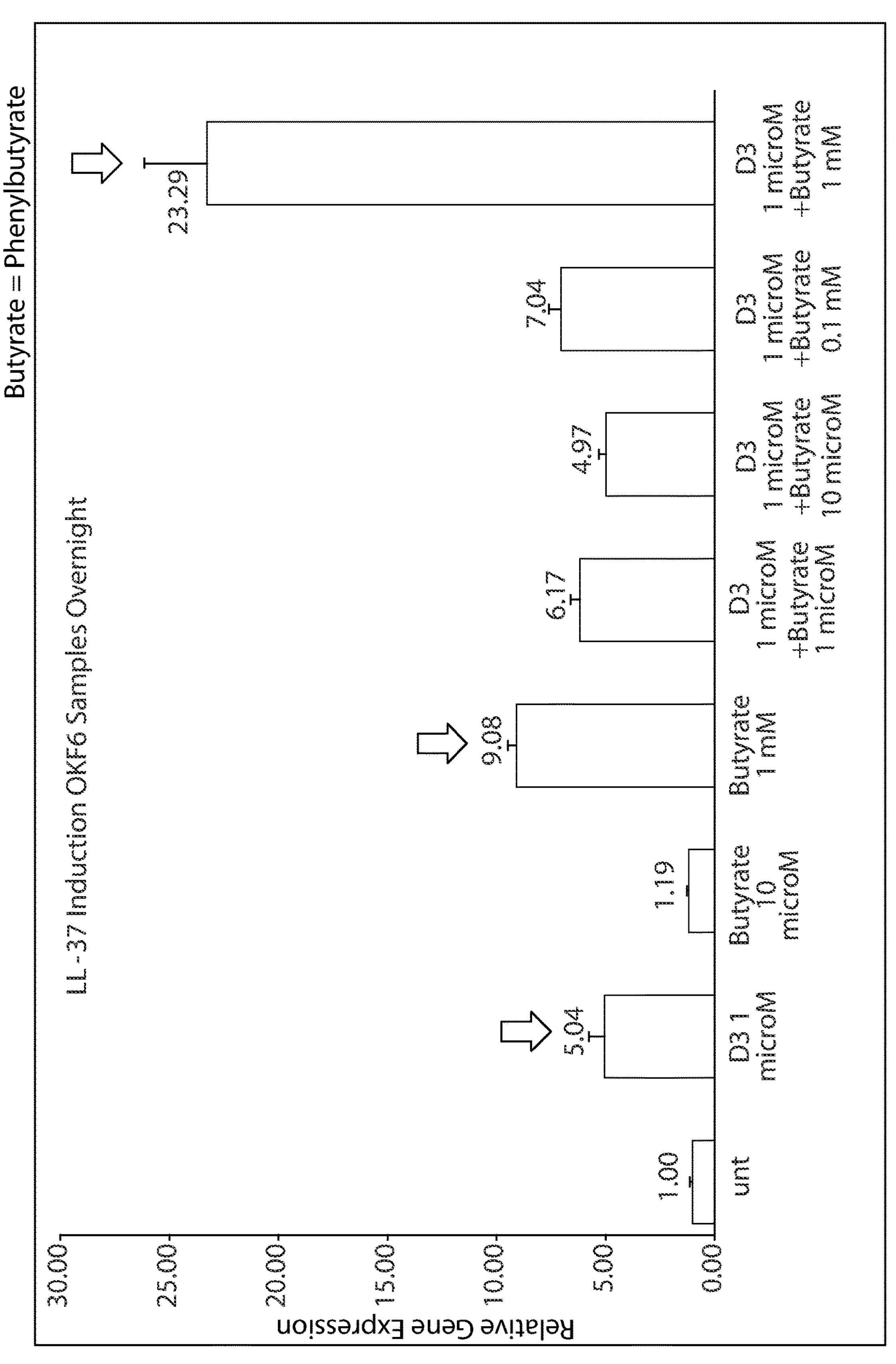
FIG. 1 depicts the LL-37 induction provided by certain embodiments of the present invention.

For illustrative purposes, the principles of the present invention are described by referencing various exemplary embodiments thereof. Although certain embodiments of the invention are specifically described herein, one of ordinary skill in the art will readily recognize that the same principles are equally applicable to, and can be employed in, other embodiments. Before explaining the disclosed embodiments of the present invention in detail, it is to be understood that the invention is not limited in its application to the details of any particular embodiment shown. The terminology used herein is for the purpose of description and not of limitation.

As used herein and in the appended claims, the singular forms "a", "an", and "the" include plural references unless the context dictates otherwise. The singular form of any class of the ingredients refers not only to one chemical species within that class, but also to a mixture of those chemical species; for example, the term "vitamin D" in the singular form, may refer to a mixture of compounds each of which is also considered a vitamin D. The terms "a" (or "an"), "one or more" and "at least one" may be used interchangeably herein. The terms "comprising", "including", and "having" may be used interchangeably. The term "include" should be interpreted as "include, but are not limited to". The term "including" should be interpreted as "including, but are not limited to".

The abbreviations and symbols as used herein, unless indicated otherwise, take their ordinary meaning. The abbreviation "wt %" means percent by weight. The symbol "μL" refers to a microliter, or $10^{-6}$ liters. The symbol "°" refers to a degree, including a degree of an angle and degree of Celsius.

When referring to chemical structures, and names, the symbols "C", "H", and "O" mean carbon, hydrogen, and oxygen, respectively. The symbols "—" and "=" mean single bond, and double bond, respectively.

The abbreviations "dy", "mo", "ppm", "PBS", "c-DNA", "RNA", "qPCR", "GAPDH", "USP", "EP", "FD&C", "pH" mean "days", "months", "parts per million", "phosphate-buffered saline" "complementary deoxyribonucleic acid", "ribonucleic acid", "quantitative polymerase chain reaction", "glyceraldehyde 3-phosphate dehydrogenase", "United States Pharmacopeia", "European Pharmacopeia", "Food, Drug & Cosmetics", negative logarithm of the molar concentration of hydronium ions, respectively.

For the ease of readability, vitamin $D_1$, vitamin $D_2$, vitamin $D_3$, vitamin $D_4$, and vitamin $D_5$ are typeset as vitamin D1, vitamin D2, vitamin D3, vitamin D4, and vitamin D5, respectively.

The term "about" when referring to a number means any number within a range of 10% of the number. For example, the phrase "about 0.050 wt %" refers to a number between and including 0.04500 wt % and 0.05500 wt %.

As used throughout, ranges are used as shorthand for describing each and every value that is within the range. Any value within the range can be selected as the terminus of the range.

The term "mixture" is to be interpreted broadly. It refers to a mixture of ingredients. The mixture may be a solid, liquid, semisolid. If a mixture is a liquid, a mixture may be a solution, an emulsion, a dispersion, a mixture displaying the Tyndall effect, or any other homogeneous mixture. Under one embpdment, the mixture is shelf stable. When referring to a list of ingredients, unless specifically indicated otherwise, the term "mixture" refers to a mixture of the aforementioned ingredients with each other, a mixture of any of aforementioned ingredients with other ingredients that are not aforementioned, and to a mixture of several aforementioned ingredients with other ingredients that are not aforementioned. For example, the term "mixture" in the phrase "the fluoride source is selected from the group consisting of stannous fluoride, sodium fluoride, amine fluoride, sodium monofluorophosphate, and mixtures thereof" refers to any of the following: a mixture of stannous fluoride and sodium fluoride; or a mixture of stannous fluoride and amine fluoride; or a mixture of stannous fluoride and sodium monofluorophosphate; or a mixture of sodium fluoride and amine fluoride; or a mixture of sodium fluoride and sodium monofluorophosphate; or a mixture of amine fluoride, sodium monofluorophosphate; or a mixture of stannous fluoride and any other fluoride source; or a mixture of sodium fluoride and any other fluoride source; or a mixture of amine fluoride and any other fluoride source; or a mixture of sodium monofluorophosphate and any other fluoride source, and other combinations thereof.

Any member in a list of species that are used to exemplify or define a genus may be mutually different from, or overlapping with, or a subset of, or equivalent to, or nearly the same as, or identical to, any other member of the list of species. Further, unless explicitly stated, such as when reciting a Markush group, the list of species that define or exemplify the genus is open, and it is given that other species may exist that define or exemplify the genus just as well as, or better than, any other species listed.

All references cited herein are hereby incorporated by reference in their entireties. In the event of a conflict in a definition in the present disclosure and that of a cited reference, the present disclosure controls.

The present invention is directed to an oral care composition comprising—in relevant part—vitamin D, or a derivative thereof.

In some embodiment, the present invention provides oral care compositions further comprising a humectant (e.g. sorbitol or glycerin and the like). In some embodiments, the humectant comprises from about 30 wt % to about 80 wt % of the oral care composition. In other embodiments, the humectant comprises from about 40 wt % to about 70 wt % of the oral care composition. In still other embodiments, the humectant comprises from about 50 wt % to about 60 wt % of the oral care composition.

In some embodiments, the oral care compositions of the present invention comprise from about 10 wt % to about 70 wt %, water, optionally from about 15 wt % to about 65 wt %, or from about 20 wt % to about 60 wt %, or from about 25 wt % to about 55 wt %, or from about 30 wt % to about 50 wt %, or from about 35 wt % to about 45 wt %, water.

In some embodiments, the compositions of the present invention comprise an abrasive. In some embodiments, the abrasive comprises a silica. In some embodiments, the silica particle may be prepared by any means known or to be developed in the art, and may be surface modified, if desired, to increase the capacity of the particle to adhere to a tooth surface. Examples may be found in, e.g., U.S. Patent Application Publication No. 20070104660, the contents of which are incorporated herein by reference. The silica particle is present in the composition in an amount of 5% or greater by weight of the total composition. Alternatively, the silica particle may be present in an amount of 5%, 6%, 7%, 8%, 9%, 10%, 15%, 20% or 25% by a weight.

In some embodiments, the silica comprises precipitated silica. Precipitated silica is an amorphous form of silica (silicon dioxide, $SiO_2$), which is a white, powdery material. Precipitated silica may be produced by precipitation from a solution containing silicate salts.

In some embodiments, the oral care compositions of the present invention comprise a thickening agent (e.g. fumed silica). Other thickening agents known to those skilled in the art may also be suitable for use in the compositions of the present invention.

In some embodiments, the particle size of the fumed silica is from about 5 nm to about 50 nm. In some embodiments, the fumed silica particles are non-porous and have a surface area of 50-600 m2/g. In other embodiments, the fumed silica has a density of 160-190 kg/m3.

Examples of silica include ZEODENT® 105-High, ZEODENT® 103, ZEODENT® 113, ZEODENT® 115, ZEODENT® 116, ZEODENT®117, ZEODENT® 120, ZEODENT® 124, ZEODENT® 153, ZEODENT® 163, ZEODENT® 165, ZEODENT® 167, ZEODENT® 168, ZEODENT® 203, ZEODENT®9175, available from Evonik; SYLODENT® 750 Silica, SYLODENT® 753 Silica, SYLODENT® 756 Silica, SYLOBLANC® 81 Silica, SYLODENT® SM 850C Silica, SYLOBLANC® 82 Silica, SYLODENT® SM 500T Silica, SYLODENT® SM 614T Silica, available from W. R. Grace; Tixosil® 63, Tixosil® 73, Tixosil® SoftClean™, Tixosil® 331, Tixosil® 43, available from Solvay; SORBOSIL AC33, SORBOSIL AC43, SORBOSIL BFG10, SORBOSIL BFG50, SORBOSIL BFG51, SORBOSIL BFG52, SORBOSIL BFG54, SORBOSIL CBT60S, SORBOSIL CBT70, SORBOSIL BFG100, available from PQ Corporation.

In some embodiments, the silica comprises Sorbosil AC43 silica, available from PQ Corporation. In an embodiment, AC43 silica has properties including, an average particle size of 2.7 to 4.0 microns (as determined by MALVERN MASTERSIZER), a sieve residue of +45 μm, a moisture loss at 105° C. of 8.0% max, an ignition loss at 1000° C. of 14.0% max, and a pH of 5.5 to 7.5 in aqueous suspension.

Under one embodiment, the thickener silica is a synthetic amorphous precipitated material of high surface area and internal pore volume to provide water absorption of about 50 ml or greater/20 grams of silica and oil absorption of about 200 ml or greater/100 g silica (per ASTM D281 method). Examples of thickener silicas which may be used are Zeodent® 165, Zeodent® 163 and Zeodent® 153; Aerosil® 200 and Sident® 22S (available from Evonik); Sylodent® 15 and Perkasil® SM 660 (available from W.R. Grace & Co.); MFIL®, MFIL® (available from Madhu Silica, India) and Tixocil 43B (available from Rhodia).

Under one embodiment, suitable silica particles for oral compositions of the invention include silica particles with, for example, a particle size distribution of 3 to 4 microns, or alternatively, a particle size distribution of 5 to 7 microns, alternatively, a particle size distribution of 3 to 5 microns, alternatively, a particle size distribution of 2 to 5 microns, or alternatively, a particle size distribution of 2 to 4 microns.

In an embodiment, a silica particle has a particle size of 2.0 microns. In another embodiment, a silica particle has a particle size of 2.5 microns. In another embodiment, a silica particle has a particle size of 3.0 microns. In another embodiment, a silica particle has a particle size of 3.5 nm microns. In another embodiment, a silica particle has a particle size of 4.0 microns. In another embodiment, a silica particle has a particle size of 4.5 microns. In another embodiment, a silica particle has a particle size of 5.0 microns. In an aspect of the invention, the silica particle size is a median particle size. In another aspect, the silica particle size is an average (mean) particle size. In an embodiment, the silica particle comprises at least 5%, at least 10%, at least 15%, at least 20%, at least 25%, at least 30%, at least 35%, or at least 40% of the total silica particles in a silica particle-containing composition. In an aspect of the invention, the silica particles have a porosity of less than about 0.45 cc/g in pores of about 600 Angstroms or smaller.

In some embodiments, the present invention is directed to an oral care composition comprising vitamin D, or a derivative thereof. In some embodiments, the vitamin D, or derivative thereof, is selected from the group consisting of:

vitamin D1, ergocalciferol, lumisterol, vitamin D2, vitamin D3, cholecalciferol, vitamin D4, 22-dihydroergocalciferol, vitamin D5, sitocalciferol, calcitriol, vitamin D compounds with hydroxyl groups at 1, 3 and 25 carbon positions, esters of 1α,25-dihydroxy vitamin D3, esters of 1,25-dihydroxy vitamin D3, 1,25 $(OH)_2D3$ analogs of $1,25(OH)_2D3$, 25(OH)D3, analogs of 25(OH)D3 and mixtures thereof. In some embodiments, the vitamin D, or derivative thereof, is selected from the group consisting of vitamin D1, ergocalciferol, lumisterol, vitamin D2, vitamin D3, cholecalciferol, vitamin D4, 22-dihydroergocalciferol, vitamin D5, sitocalciferol, calcitriol, and mixtures thereof. In other embodiments, the vitamin D, or derivative thereof, is cholecalciferol.

In some embodiments, the vitamin D, or derivative thereof, is any one of a group of fat-soluble secosteroids that may be used to increase intestinal absorption of calcium, magnesium, and phosphate, and multiple other biological effects. The major natural source of the vitamin is synthesis of cholecalciferol in the skin from cholesterol through a chemical reaction that is dependent on sun exposure (specifically radiation at about 280-315 nm).

In certain embodiments, vitamin D, or a derivative thereof, refers to compounds that include: vitamin D1, vitamin D2, vitamin D3, vitamin D4, vitamin D5, vitamin D compounds with hydroxyl groups at 1, 3 and 25 carbon positions, esters of 1α,25-dihydroxy vitamin D3, esters of 1,25-dihydroxy vitamin D3, $1,25(OH)_2D3$ analogs of 1,25 $(OH)_2D3$, calcitriol, 25(OH)D3, analogs of 25(OH)D3 and any mixture thereof.

The term "Vitamin D" under one embodiment means any one compounds of vitamin D1, vitamin D2, vitamin D3, vitamin D4, vitamin D5, or any combination thereof.

Vitamin D1 is a mixture of molecular compounds of ergocalciferol and lumisterol. Under one embodiment, vitamin D1 is a 1:1 mixture of ergocalciferol and lumisterol. Vitamin D2 is or comprises ergocalciferol, or calciferol. Vitamin D2 is a type of vitamin D found in food and used as a dietary supplement used to prevent and treat vitamin D deficiency. Such vitamin D deficiency may be due to poor absorption by the intestines or liver disease. Vitamin D2 may also be used for low blood calcium due to hypoparathyroidism. Ergocalciferol has the formula

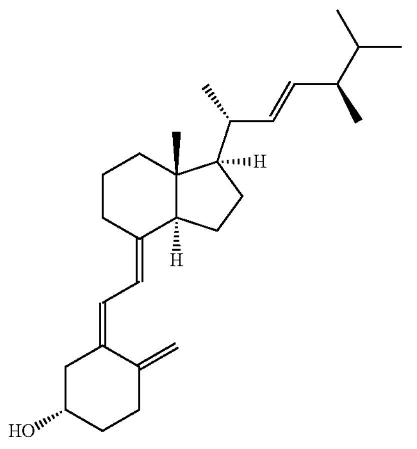 [SMILES: C=C1CC[C@H](O)C/C1=C/C=C1\CCC[C@]2(C)[C@@H]([C@H](C)/C=C/[C@H](C)C(C)C)CC[C@@H]12]

Vitamin D3 is, or comprises, cholecalciferol, also known as colecalciferol. Cholecalciferol is a type of vitamin D which is made by the skin when exposed to sunlight; it is also found in some foods and can be taken as a dietary supplement. Cholecalciferol is used to treat diseases associated with vitamin D deficiency (including rickets), familial hypophosphatemia, hypoparathyroidism that is causing low blood calcium, and Fanconi syndrome. Cholecalciferol has the structure

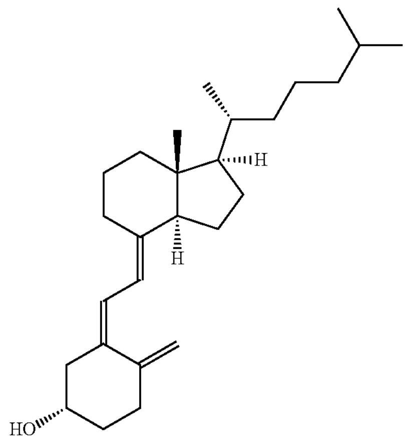 [SMILES: C=C1CC[C@H](O)C/C1=C/C=C1\CCC[C@]2(C)[C@@H]([C@H](C)CCCC(C)C)CC[C@@H]12]

Cholecalciferol is made in the skin following UV-B (about 280-315 nm) light exposure. Cholecalciferol is converted in the liver to calcifediol, i.e., 25-hydroxyvitamin D, which is then converted in the kidney to calcitriol, i.e., 1,25-dihydroxyvitamin D. One of the actions of cholecalciferol is to increase the uptake of calcium by the intestines. Cholecalciferol is found in food such as some fish, cheese, and eggs.

Cholecalciferol by itself is inactive. It is converted to its active form by two hydroxylations: the first in the liver, by CYP2R1 or CYP27A1, to form 25-hydroxycholecalciferol (calcifediol, 25-OH vitamin D3). The second hydroxylation occurs mainly in the kidney through the action of CYP27B1 to convert 25-OH vitamin D3 into 1,25-dihydroxycholecalciferol (calcitriol, 1,25-(OH)2vitamin D3). All these metabolites are bound in blood to the vitamin D-binding protein. The action of calcitriol is mediated by the vitamin D receptor, a nuclear receptor which regulates the synthesis of hundreds of proteins and is present in virtually every cell in the body.

Vitamin D4 is 22-dihydroergocalciferol, with the structure

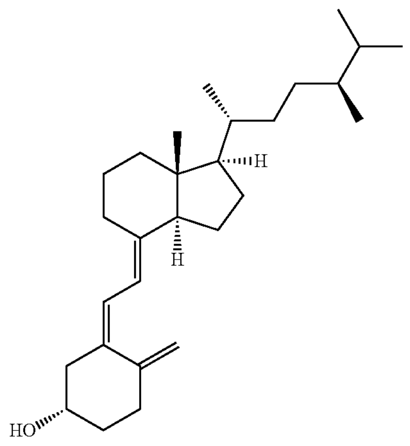 [SMILES: C=C1CC[C@H](O)C/C1=C/C=C1\CCC[C@]2(C)[C@@H]([C@H](C)CC[C@H](C)C(C)C)CC[C@@H]12]

Vitamin D5 is sitocalciferol, with the structure:

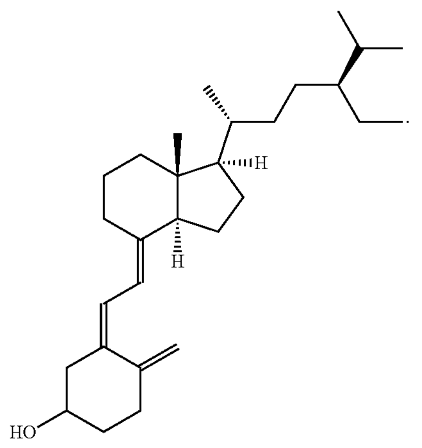 [SMILES: C=C1CCC(O)C/C1=C/C=C1\CCC[C@]2(C)[C@@H]([C@H](C)CC[C@H](CC)C(C)C)CC[C@@H]12]

As vitamin D3 can be synthesized in adequate amounts by most mammals exposed to sufficient sunlight, it is not an essential dietary factor, and so not technically a vitamin. Instead, vitamin D could be considered a hormone, with activation of the vitamin D pro-hormone resulting in the active form, calcitriol, which then produces effects via a nuclear receptor in multiple locations. Cholecalciferol is converted in the liver to calcifediol (25-hydroxycholecalciferol); ergocalciferol is converted to 25-hydroxyergocalciferol. These two vitamin D metabolites (called 25-hydroxyvitamin D or 25(OH)D) are measured in serum to determine a person's vitamin D status. Calcifediol is further hydroxylated by the kidneys to form calcitriol (also known as 1,25-dihydroxycholecalciferol), the biologically active form of vitamin D. Calcitriol circulates as a hormone in the blood, having a major role regulating the concentration of calcium and phosphate, and promoting the healthy growth and remodeling of bone. Calcitriol also has other effects, including some on cell growth, neuromuscular and immune functions, and reduction of inflammation.

Incipient periodontal inflammation, gingivitis, is known to result from the inflammation reaction to the endotoxins released by the presence of bacterial biofilms in the general area of the tooth anatomy. Left untreated, this condition frequently progresses to the more virulent pathological condition known as periodontitis. Frequent use of vitamin D, topical, supplement compositions of the invention provides protection by forming mucoadhesive gels that continuously release vitamin D composition at the inflamed site; thereby inducing passive diffusion of vitamin D into the mucosa which, in turn, increases production of the antimicrobial peptides and provokes a putative therapeutic immune modulating response.

Periodontal diseases are initiated by a consortia of oral bacteria that elicit local inflammatory responses that lead to bleeding on probing, loss of periodontal attachment, as well as bone and tooth loss. They have been linked to systemic conditions, including heart disease, diabetes, obesity and metabolic syndrome. The association between periodontal diseases and these systemic conditions seems to be due to a low grade inflammatory burden that links them through a common pathophysiological mechanism. Conceivably, locally secreted cytokines and periodontal pathogens can enter into the bloodstream and contribute to damage elsewhere in the body and there appears to be some evidence for that burden.

Tumor necrosis factor α (TNF-α) and interleukin 6 (IL-6) are key cytokines in the initiation and maintenance of systemic inflammation which have been implicated in progression and severity of periodontitis. In addition, higher serum levels of these cytokines have been observed in periodontitis patients than in periodontally healthy individuals.

Vitamin D has an important role in bone growth and maintenance, which might be beneficial for maintaining periodontal health. Recently, it has been suggested to have positive effects on periodontal diseases, tooth loss and gingival inflammation not through its effects on bone metabolism, but rather through anti-inflammatory mechanisms. Hence, maintaining adequate serum values of Vitamin D via topical, adjunctive, vitamin D supplement compositions could be important in the prevention and treatment of periodontal diseases.

Vitamin D has an important role in calcium homeostasis, bone growth and preservation. It has been shown to inhibit antigen-induced T cell proliferation and cytokine production, acting as an immunomodulatory agent.

Under one embodiment, the present invention provides an oral care composition which may be used to prevent a pathological condition by boosting host tissue antimicrobial peptides (AMPs) in the oral cavity.

Antimicrobial peptides, also called host defense peptides, play an important part of the innate immune response found among all classes of life. Fundamental differences exist between prokaryotic and eukaryotic cells that may represent targets for antimicrobial peptides. Such peptides may be potent, broad-spectrum antibiotics which demonstrate potential as novel therapeutic agents. Antimicrobial peptides may kill Gram negative bacteria, Gram positive bacteria, enveloped viruses, fungi. Antimicrobial peptides may have an antimicrobial and mediator function and provide the initial host defense mechanism. Unlike the majority of conventional antibiotics antimicrobial peptides may destabilize biological membranes, can form transmembrane channels, and may also have the ability to enhance immunity by functioning as immunomodulators. Further, in addition to antimicrobial defense, antimicrobial peptides have an important role in wound healing, anti-inflammation strengthens the physical barrier of oral mucosa by enhancing tissue integrity and tissue regeneration.

Further, an antimicrobial peptide is a peptide that exhibits antimicrobial activity or a compound that affects microbial activity, meaning a compound that slows or stops the growth and/or proliferation, slows or stops the rate of growth and/or proliferation, or stuns, inactivates, or kills a microbe. Examples of antimicrobial peptides include antibiotics, antibacterials, (e.g., bactericidal or bacteriostatic agents), antivirals (e.g., virucidal agents), antifungals (e.g., fungicidal or fungistatic agents), mold-inhibiting agents, anthelminthics (e.g., vermifuge or vermicidal agents), antiparasitics, and the like. Antimicrobial activity can be determined using methods described herein as well as methods known in the art.

Under one embodiment, the present invention is directed to a method of boosting host tissue antimicrobial peptide in the oral cavity by applying toothpaste to a portion of the oral cavity, wherein the toothpaste comprises the oral care composition comprising: sorbitol solution, silica, and vitamin D.

The data demonstrate that topical application of the active form of vitamin D ($1,25(OH)_2D3$) to of gingival epithelial cells (GEC) induces enhanced expression of Anti-microbial peptide (LL-37) proteins and thus helps in maintaining innate defense in oral gingival cells. This active form of Vitamin D3 (1,25(OH)2D3), however, is unstable and expensive. Conventional biology contends that inactive vitamin D (cholecalciferol) is converted to 25(OH)D3 by 25-hydroxylase enzymes found in the liver, and that circulating form is further activated by the 1-α hydroxylase enzyme to the active form, 1,25(OH)2D3, in the kidney.

The data shows that GEC are capable of converting the inactive forms to the active form as well. Therefore, it is hypothesized that topical application of vitamin D, both inactive and active, directly to the GEC, can lead to an overall therapeutic effect on the etiology and development of the periodontal disease. The data shows a boost expression of LL-37 on gingival cells by both inactive and active form of Vitamin D3.

Analytical HPLC stability data demonstrate 100% stable Vitamin D3 recovery from toothpaste formulation, both in fresh and 2 months aged samples.

Under one embodiment, the present invention is directed to an oral care composition comprising: sorbitol solution, silica; and vitamin D, wherein the oral care composition comprises between about 0.001 wt % and about 0.100 wt % vitamin D.

Under one embodiment, the oral care composition comprises from about 0.001 wt % to about 0.003 wt % vitamin D. Under one embodiment, the oral care composition comprises from about 0.001 wt % to about 0.005 wt % vitamin D. Under one embpdment, the oral care composition comprises from about 0.001 wt % to about 0.01 wt % vitamin D. Under one embodiment, the oral care composition comprises from about 0.001 wt % to about 0.03 wt % vitamin D. Under one embodiment, the oral care composition comprises from about 0.001 wt % to about 0.05 wt % vitamin D. Under one embodiment, the oral care composition comprises from about 0.001 wt % to about 0.1 wt % vitamin D.

Under one embodiment, the oral care composition comprises from about 0.003 wt % to about 0.005 wt % vitamin D. Under one embodiment, the oral care composition comprises from about 0.003 wt % to about 0.01 wt % vitamin D. Under one embodiment, the oral care composition comprises from about 0.003 wt % to about 0.03 wt % vitamin D. Under one embodiment, the oral care composition comprises from about 0.003 wt % to about 0.05 wt % vitamin D. Under one embodiment, the oral care composition comprises from about 0.003 wt % to about 0.1 wt % vitamin D.

Under one embodiment, the oral care composition comprises from about 0.005 wt % to about 0.01 wt % vitamin D. Under one embodiment, the oral care composition comprises from about 0.005 wt % to about 0.03 wt % vitamin D. Under one embodiment, the oral care composition comprises from about 0.005 wt % to about 0.05 wt % vitamin D. Under one embodiment, the oral care composition comprises from about 0.005 wt % to about 0.1 wt % vitamin D.

Under one embodiment, the oral care composition comprises from about 0.01 wt % to about 0.03 wt % vitamin D. Under one embodiment, the oral care composition comprises from about 0.01 wt % to about 0.05 wt % vitamin D. Under one embodiment, the oral care composition comprises from about 0.01 wt % to about 0.1 wt % vitamin D.

Under one embodiment, the oral care composition comprises from about 0.03 wt % to about 0.05 wt % vitamin D. Under one embodiment, the oral care composition comprises from about 0.03 wt % to about 0.1 wt % vitamin D. Under one embodiment, the oral care composition comprises from about 0.05 wt % to about 0.1 wt % vitamin D.

The present invention is also directed to an oral care composition comprising sorbitol solution, silica; and vitamin D, wherein the oral care composition further comprises a toothpaste ingredient selected from: a surfactant, a desensitizing agent, a hydrophilic polymer, a tartar control agent, a binder, a thickening agents, a detergent, an adhesion agents, a foam modulator, a pH modifying agent, a mouth feel agent, a sweetener, a flavorants, a coloring agent, a humectant, a fluoride source, and a mixture thereof a viscosity modifier, and a mixture thereof.

Under one embodiment, the present invention is directed to an oral care composition comprising: sorbitol solution, silica; and vitamin D, wherein the oral care composition further comprises a blue coloring agent.

Orally acceptable blue coloring agent comprises a blue dye which is safe for use in oral care applications, and include blue dyes from natural sources as well as synthetic dyes approved for use in foods or oral care products, e.g. FD&C Blue No. 1 and FD&C Blue No. 2. Dyes for use in the present invention to prepare the water-insoluble whitening complex may be water soluble. The term "water-soluble" in this particular context generally means that the dye has an aqueous solubility of at least 10 g/L at 25.degree. C., most preferably at least 100 g/L at 25.degree. C. (where the solubility is determined in un-buffered distilled water).

In particular embodiments, oral care composition dyes useful herein have a maximum absorbance value in the visible spectrum ($\lambda_{max}$) at a wavelength ranging from 550 nm to 650 nm, more preferably from 600 nm to 650 nm. Dyes useful herein may have a blue to blue-green color with a hue angle in the CIELAB system ranging from 180 to 270 degrees, more particularly 180 to 200 degrees. Dyes useful herein include anionic triphenylmethane dyes, and especially diaminotriphenylmethane dyes containing from two to four sulphonate groups, An example of a dye useful herein is FD&C Blue #1, also known as Brilliant Blue FCF (Blue 1) as well as other commercial names. FD&C Blue #1 is a colorant for foods and other substances to induce a color change. It is denoted by E number E133 and has a color index of 42090. It has the appearance of a reddish-blue powder. It is soluble in water, and the solution has a maximum absorption at about 628 nanometers. It is a synthetic dye produced using aromatic hydrocarbons from petroleum. It is usually a disodium salt. The diammonium salt has CAS number [2650-18-2]. Calcium and potassium salts are also known.

Additional dyes may be used in conjunction with the blue dye, in order to adjust the precise color absorption as desired.

The present invention is also directed to an oral care composition comprising sorbitol solution, silica; and vitamin D, wherein the oral care composition further comprises a toothpaste ingredient selected from: a surfactant, a desensitizing agent, a hydrophilic polymer, a tartar control agent, a binder, a thickening agents, a detergent, an adhesion agents, a foam modulator, a pH modifying agent, a mouth feel agent, a sweetener, a flavorants, a coloring agent, a humectant, a fluoride source, a viscosity modifier, and a mixture thereof, wherein the coloring agent is a blue coloring agent that has a blue to blue-violet color with a hue angle in the CIELAB system ranging from 200 degrees to 320 degrees. [11109]

The present invention is also directed to an oral care composition comprising sorbitol solution, silica; and vitamin D, wherein the oral care composition further comprises a toothpaste ingredient selected from: a surfactant, a desensitizing agent, a hydrophilic polymer, a tartar control agent, a binder, a thickening agents, a detergent, an adhesion agents, a foam modulator, a pH modifying agent, a mouth feel agent, a sweetener, a flavorants, a coloring agent, a humectant, a fluoride source, a viscosity modifier, and a mixture thereof, wherein the blue coloring agent is a blue dye present in an amount of from about 0.02 wt % to about 2 wt %, based on the total amount of the oral care composition.

The present invention is also directed to an oral care composition comprising sorbitol solution, silica; and vitamin D, wherein the oral care composition further comprises a toothpaste ingredient selected from: a surfactant, a desensitizing agent, a hydrophilic polymer, a tartar control agent, a binder, a thickening agents, a detergent, an adhesion agents, a foam modulator, a pH modifying agent, a mouth feel agent, a sweetener, a flavorants, a coloring agent, a humectant, a fluoride source, a viscosity modifier, and a mixture thereof, wherein the blue coloring agent comprises at least one of FD&C Blue #1, FD&C Blue #2, D&C Blue #4, CI Food Blue 5, and Acid Blue 1.

As used herein, the term "blue coloring agent" refers to a substance in the form of a dry powder or liquid that imparts color to another substance. Generally, coloring agents include pigments, dyes, lakes, or combinations thereof.

In an aspect, the blue coloring agent has a blue to blue-violet color with a hue angle in the CIELAB system ranging from 200 degrees to 320 degrees.

In some embodiments, the whitening dentifrice compositions of the present disclosure may include a pigment. As used herein, a "pigment" is a synthetic or natural water insoluble substance, which imparts color to another substance. In some embodiments, the pigments further enhance the whiteness of the teeth. As is known in the art, the visual perception of a white substance can be altered through the deposition of an optical brightener, a blue pigment, or a blue dye. This effect is commonly used in laundry detergent products to make white clothes appear "whiter" to the human eye. The same concept has been applied to tooth whitening. See PCT Publication No. WO 2015/099642 to Colgate-Palmolive Company, which is herein incorporated by reference in its entirety.

In some embodiments, the pigment included in the whitening dentifrice compositions of the present disclosure may have a hue angle, h, in the CIELAB system ranging from 220 degrees to 320 degrees, typically between 250 degrees and 290 degrees.

The pigment used in the whitening dentifrice compositions is capable of reflecting sufficient light such that the treated tooth is perceivably whiter than its initial color. In some embodiments, the pigment may be colored such that its natural color is within the violet-red to green-blue color. More particularly, the pigment may be violet or blue, e.g., one of those listed in the Color Index International. These pigments are listed as violet pigment #1 through to #56 and blue pigment #1 through #83. In some embodiments, the violet pigment may be violet pigment #1, 1:1, 1:2, 2, 3, 5:1, 13, 19, 23, 25, 27, 31, 32, 37, 39, 42, 44 and/or 50. In some embodiments, the blue pigments may be blue pigment #1, 2, 9, 10, 14, 15, 15:1, 15:2, 15:3, 15:4, 15:6 16, 18, 19, 24:1, 25, 56, 60, 61, 62 and/or 66. Other suitable pigments are pigment ultramarine blue and ultramarine violet. Typically, the pigment is blue pigment #15, more typically blue pigment #15:1, 15:2, 15:3, 15:4, 15:5 or 15:6, most typically 15:1.

While blue or violet single pigments may be used in the whitening dentifrice compositions, the same effect may be achieved through mixing pigments outside of the hue angle range of 220 degrees to 320 degrees. The desired hue angle may instead be obtained by mixing a red and green-blue pigment to yield a blue or violet shaded pigment.

The amount of pigment in the whitening dentifrice composition may be from 0.01 to 0.075 weight %, such as 0.05%. In other embodiments, the amount of pigment in the whitening dentifrice composition may be from 0.01 to 0.05 weight %, or from 0.03 to 0.05%, by weight based on the total amount of the whitening dentifrice composition. The pigment may be uniformly spread throughout the whitening dentifrice composition or may be dispersed in a second phase such as a stripe or other coextruded second phase. Such "dual phase" compositions have the advantage that the phases may be differently colored, presenting a more visually attractive product to the consumer.

As used herein, the term "dye" refers to an organic species, which is essentially water soluble in an aqueous medium in which the dye remains chemically stable. The dyes used with the whitening dentifrice composition of the present disclosure are generally food color additives presently certified under the Food Drug & Cosmetic Act for use in food and ingested drugs, including dyes such as FD&C Red No. 3 (sodium salt of tetraiodofluorescein), FD&C Yellow No. 5 (sodium salt of 4-p-sulfophenylazo-1-p-sulfophenyl-5-hydroxypyrazole-3 carboxylic acid), FD&C Yellow No. 6 (sodium salt of p-sulfophenylazo-B-naphtol-6-monosulfonate), FD&C Green No. 3 (disodium salt of 4-{[4-(N-ethyl-p-sulfobenzylamino)-phenyl]-(4-hydroxy-2-sulfonium-phenyl)-methylene}-[1-N-ethyl-N-p-sulfobenzyl)-.DELTA.-3,5-cyclohexadienimine], FD&C Blue No. 1 (disodium salt of dibenzyldiethyl-diaminotriphenylcarbinol trisulfonic acid anhydride), FD&C Blue No. 2 (sodium salt of disulfonic acid of indigotin) D&C Green No. 5, D&C Orange No. 5, D&C Red No. 21, D&C Red No. 22, D&C Red No. 27, D&C Red No. 28, D&C Red No. 30, D&C Red No. 40, D&C Yellow No. 10 and mixtures thereof in various proportions.

In an aspect, the blue coloring agent is a blue dye selected from among FD&C Blue #1, FD&C Blue #2, D&C Blue #4, CI Food Blue 5, Acid Blue 1, or a mixture thereof.

The amount of one or more of the dyes in the oral care composition may widely vary. For example, the amount of one or more of the dyes in the whitening dentifrice composition of the present disclosure may be from 0.02 to 2 weight %, or 0.02 to 1.5 weight %, or 0.02 to 1 weight %, or 0.02 to 0.5 weight %, 0.02 to 0.15 weight %, or 0.02 to 0.1 weight %, based on the total amount of the whitening dentifrice composition. In at least one embodiment, the one or more dyes may be disposed or dispersed uniformly throughout the whitening dentifrice composition. In another embodiment, the one or more dyes may be disposed or dispersed in different phases of the whitening dentifrice composition. For example, one or more of the dyes may be disposed or dispersed in a first phase (e.g., a hydrophobic phase) of the whitening dentifrice composition, and one or more of the remaining dyes, or no dye, may be disposed or dispersed in a second phase (e.g., a hydrophilic phase) of the whitening dentifrice composition.

The present invention is also directed to an oral care composition comprising sorbitol solution, silica; and vitamin D, wherein the oral care composition further comprises a toothpaste ingredient selected from: a surfactant, a desensitizing agent, a hydrophilic polymer, a tartar control agent, a binder, a thickening agents, a detergent, an adhesion agents, a foam modulator, a pH modifying agent, a mouth feel agent, a sweetener, a flavorants, a coloring agent, a humectant, a fluoride source, a viscosity modifier, and a mixture thereof, wherein the surfactant is selected from the group consisting of water-soluble salts of $C_{8-20}$ alkyl sulfates, sulfonated monoglycerides of $C_{8-20}$ fatty acids, sarcosinates, taurates, sodium lauryl sulfate, sodium cocoyl mono glyceride sulfonate, sodium lauryl sarcosinate, sodium lauryl isoethionate, sodium laureth carboxylate and sodium dodecyl benzenesulfonate, cocoamidopropyl betaine, and mixtures thereof.

Further examples of suitable surfactants include water-soluble salts of higher fatty acid monoglyceride monosulfates, such as the sodium salt of monosulfated monoglyceride of hydrogenated coconut oil fatty acids; higher alkyl sulfates such as sodium lauryl sulfate; alkyl aryl sulfonates such as sodium dodecyl benzene sulfonate; higher alkyl sulfoacetates, such as sodium lauryl sulfoacetate; higher fatty acid esters of 1,2-dihydroxypropane sulfonate; and the substantially saturated higher aliphatic acyl amides of lower aliphatic amino carboxylic compounds, such as those having 12-16 carbons in the fatty acid, alkyl or acyl radicals; and the like. Examples of the last mentioned amides include N-lauryl sarcosine, and the sodium, potassium and ethanolamine salts of N-lauryl, N-myristoyl, or N-palmitoyl sarcosine. Others include, for example, nonanionic polyoxyethylene surfactants, such as Polyoxamer 407, Steareth 30, Polysorbate 20, and castor oil; and amphoteric surfactants, such as cocamidopropyl betaine (tegobaine), and cocamidopropyl betaine lauryl glucoside; condensation products of ethylene oxide with various hydrogen containing compounds that are reactive therewith and have long hydrocarbon chains (e.g., aliphatic chains of from 12 to 20 carbon atoms), which condensation products (ethoxamers) contain hydrophilic polyoxyethylene moieties, such as condensation products of poly (ethylene oxide) with fatty acids, fatty, alcohols, fatty amides and other fatty moieties, and with propylene oxide and polypropylene oxides.

The present invention is also directed to an oral care composition comprising sorbitol solution, silica; and vitamin D, wherein the oral care composition further comprises a toothpaste ingredient selected from: a surfactant, a desensitizing agent, a hydrophilic polymer, a tartar control agent, a binder, a thickening agents, a detergent, an adhesion agents, a foam modulator, a pH modifying agent, a mouth feel agent, a sweetener, a flavorants, a coloring agent, a humectant, a fluoride source, a viscosity modifier, and a mixture thereof, wherein the viscosity modifier is selected from the group consisting of methylcellulose, hydroxypropyl methyl cellulose, hydroxyethylpropyl cellulose, hydroxybutyl methyl cellulose, carboxymethyl cellulose, salts thereof, and mixtures thereof.

In some embodiments, the compositions of the invention may optionally comprise an additional orally acceptable thickening agent, selected from one or more of, without limitation, carbomers, also known as carboxyvinyl polymers, carrageenans, also known as Irish moss and more particularly carrageenan (iota-carrageenan), high molecular weight polyethylene glycols (such as CARBOWAX®, available from The Dow Chemical Company), cellulosic polymers such as hydroxyethylcellulose, carboxymethylcellulose (CMC) and salts thereof, e.g., CMC sodium, natural gums such as karaya, xanthan, gum arabic and tragacanth, and colloidal magnesium aluminum silicate and mixtures of the same. Optionally, such additional thickening agents are present in a total amount of about 0.1 wt % to about 50 wt %, for example about 0.1 wt % to about 35 wt % or about 1 wt % to about 15 wt %, based on the weight of the composition.

The present invention is also directed to an oral care composition comprising sorbitol solution, silica; and vitamin D, wherein the oral care composition further comprises a toothpaste ingredient selected from: a surfactant, a desensitizing agent, a hydrophilic polymer, a tartar control agent, a binder, a thickening agents, a detergent, an adhesion agents, a foam modulator, a pH modifying agent, a mouth feel agent, a sweetener, a flavorants, a coloring agent, a humectant, a fluoride source, a viscosity modifier, and a mixture thereof, wherein the sweetener is selected from the group consisting of: saccharin, salts thereof, and mixtures thereof.

Under one embodiment, the composition of the invention comprises at least one sweetener, useful for example to enhance taste of the composition. Any orally acceptable natural or artificial sweetener can be used, including without limitation dextrose, sucrose, maltose, dextrin, dried invert sugar, mannose, xylose, ribose, fructose, levulose, galactose, corn syrup (including high fructose corn syrup and corn syrup solids), partially hydrolyzed starch, hydrogenated starch hydrolysate, sorbitol, mannitol, xylitol, maltitol, isomalt, aspartame, neotame, saccharin and salts thereof, dipeptide-based intense sweeteners, cyclamates and the like. One or more sweeteners are optionally present in a total amount depending strongly on the particular sweetener(s) selected, but typically 0.005 wt. % to 5 wt. %, by total weight of the composition.

The present invention is also directed to an oral care composition comprising sorbitol solution, silica; and vitamin D, wherein the oral care composition further comprises a toothpaste ingredient selected from: a surfactant, a desensitizing agent, a hydrophilic polymer, a tartar control agent, a binder, a thickening agents, a detergent, an adhesion agents, a foam modulator, a pH modifying agent, a mouth feel agent, a sweetener, a flavorants, a coloring agent, a humectant, a fluoride source, a viscosity modifier, and a mixture thereof, wherein the hydrophilic polymer is selected from the group consisting of polyethylene glycol.

The present invention is also directed to an oral care composition comprising sorbitol solution, silica; and vitamin D, wherein the oral care composition further comprises a toothpaste ingredient selected from: a surfactant, a desensitizing agent, a hydrophilic polymer, a tartar control agent, a binder, a thickening agents, a detergent, an adhesion agents, a foam modulator, a pH modifying agent, a mouth feel agent, a sweetener, a flavorants, a coloring agent, a humectant, a fluoride source, a viscosity modifier, and a mixture thereof, wherein the fluoride source is selected from the group consisting of sodium fluoride, stannous fluoride, sodium fluoride, amine fluorides, sodium monofluorophosphate, and mixtures thereof.

In some embodiments, the composition comprises a fluoride ion source. Fluoride ion sources include, but are not limited to: stannous fluoride, sodium fluoride, potassium fluoride, potassium monofluorophosphate, sodium monofluorophosphate, ammonium monofluorophosphate, sodium fluorosilicate, ammonium fluorosilicate, amine fluoride such as olaflur (N'-octadecyltrimethylendiamine-N,N,N'-tris(2-ethanol)-dihydrofluoride), ammonium fluoride, and combinations thereof. In certain embodiments the fluoride ion source includes stannous fluoride, sodium fluoride, amine fluorides, sodium monofluorophosphate, as well as mixtures thereof. In certain embodiments, the oral care composition of the invention may also contain a source of fluoride ions or fluorine-providing ingredient in amounts sufficient to supply about 50 to about 5000 ppm fluoride ion, e.g., from about 100 to about 1000, from about 200 to about 500, or about 250 ppm fluoride ion. Fluoride ion sources may be added to the compositions of the invention at a level of about 0.001 wt. % to about 10 wt. %, e.g., from about 0.003 wt. % to about 5 wt. %, 0.01 wt. % to about 1 wt., or about 0.05 wt. %. However, it is to be understood that the weights of fluoride salts to provide the appropriate level of fluoride ion will obviously vary based on the weight of the counter ion in the salt, and one of skill in the art may readily determine such amounts. A preferred fluoride salt may be sodium fluoride.

The present invention is also directed to an oral care composition comprising sorbitol solution, silica; and vitamin D, wherein the oral care composition is a toothpaste.

Under one embodiment, oral care composition is a toothpaste, a liquid, a gel, a whitening strip, or a composition which is applied to the teeth using a dental tray. In certain embodiments, the composition is a toothpaste. In some embodiments, the toothpaste is adapted to be applied to the teeth by brushing.

EXAMPLES

Example 1

Figure 2:
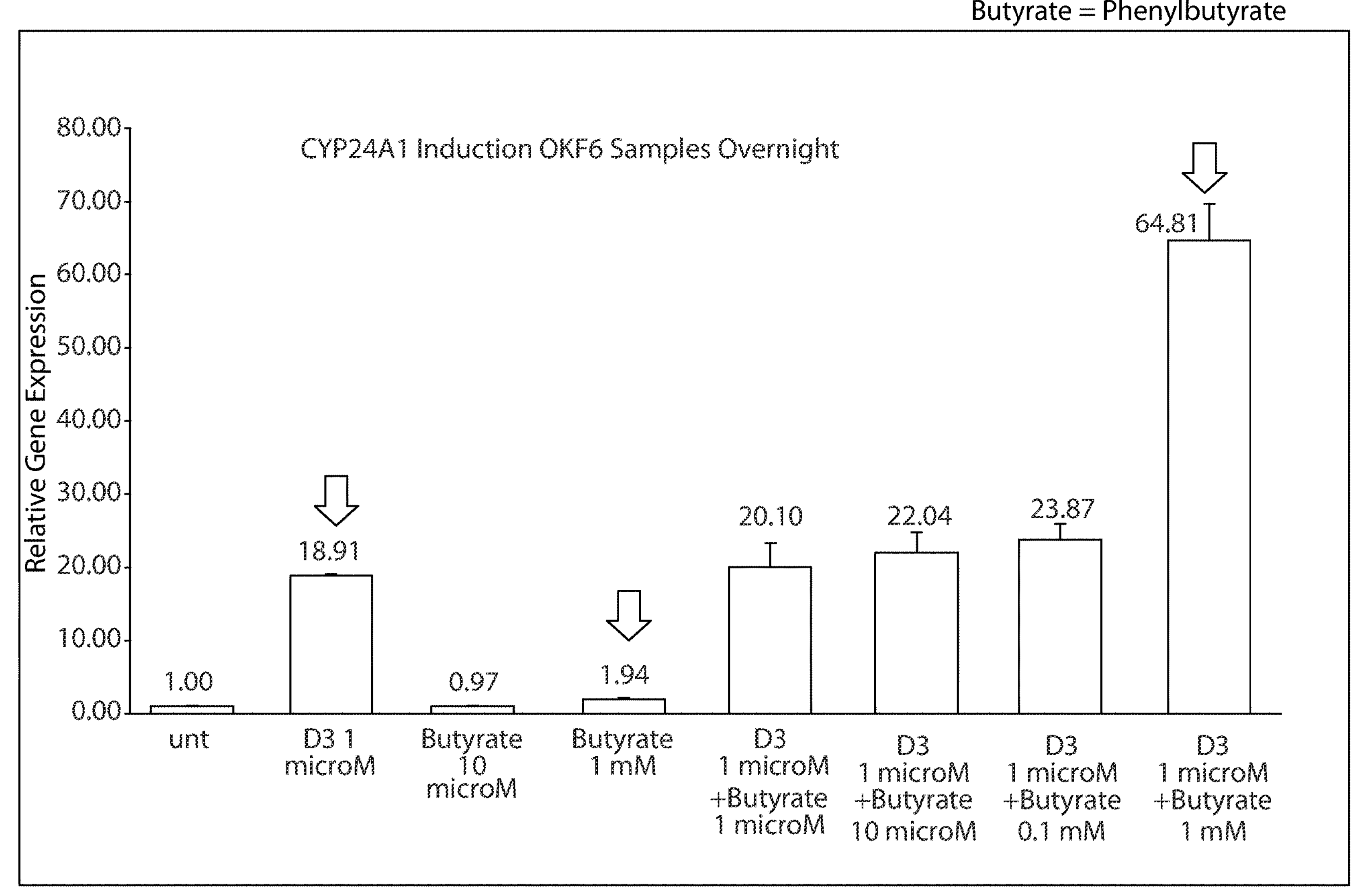
FIG. 2 depicts the CPY24A1 induction provided by certain embodiments of the present invention.

OKF6 Cells (Gingival epithelial cells) were grown in 6 well tissue culture plates. Cells monolayer was treated with indicated doses (FIG. 1) of Vitamin D3 or phenylbutyrate alone or in combinations of two and cells were further incubated in tissue culture incubator for overnight incubation. After overnight incubation, cells were harvested in RNA lysis buffer. Lysates were processed for RNA isolation using Qiagen RNA isolation kit. RNA was processed for c-DNA preparation and further amplified (qPCR) using LL-37 (Hs 01011708_m1), Cyp24A1 (Hs00989018_m1), GAPDH (Hs 99999905_m1) Taqman genes specific probes. QPCR data was analyzed for fold induction of LL-37 expression and relative difference of expressions was plotted. These results are described in FIGS. 1 and 2. As illustrated by the data described in FIGS. 1 and 2, the inventive combinations of the present invention provide a synergistic increase in LL-37 and CYP24A1, respectively.

Example 2

Figure 3A:
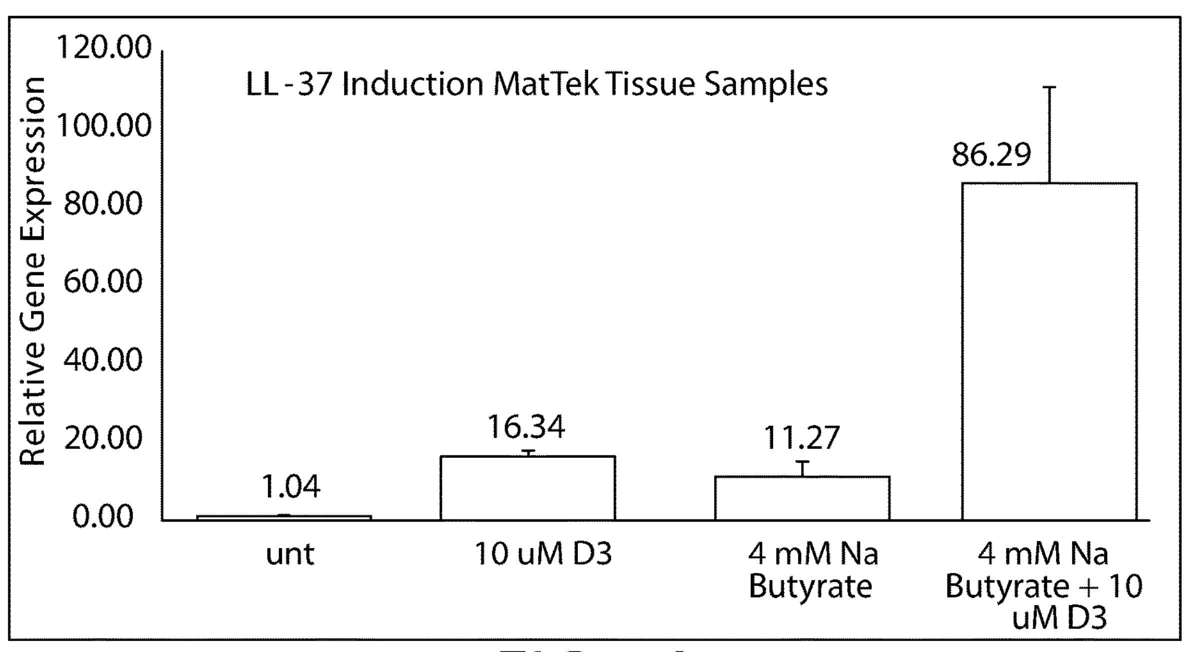
FIG. 3A and FIG. 3B depict the benefits provided by certain embodiments of the present invention in a tissue model.
Figure 3B:
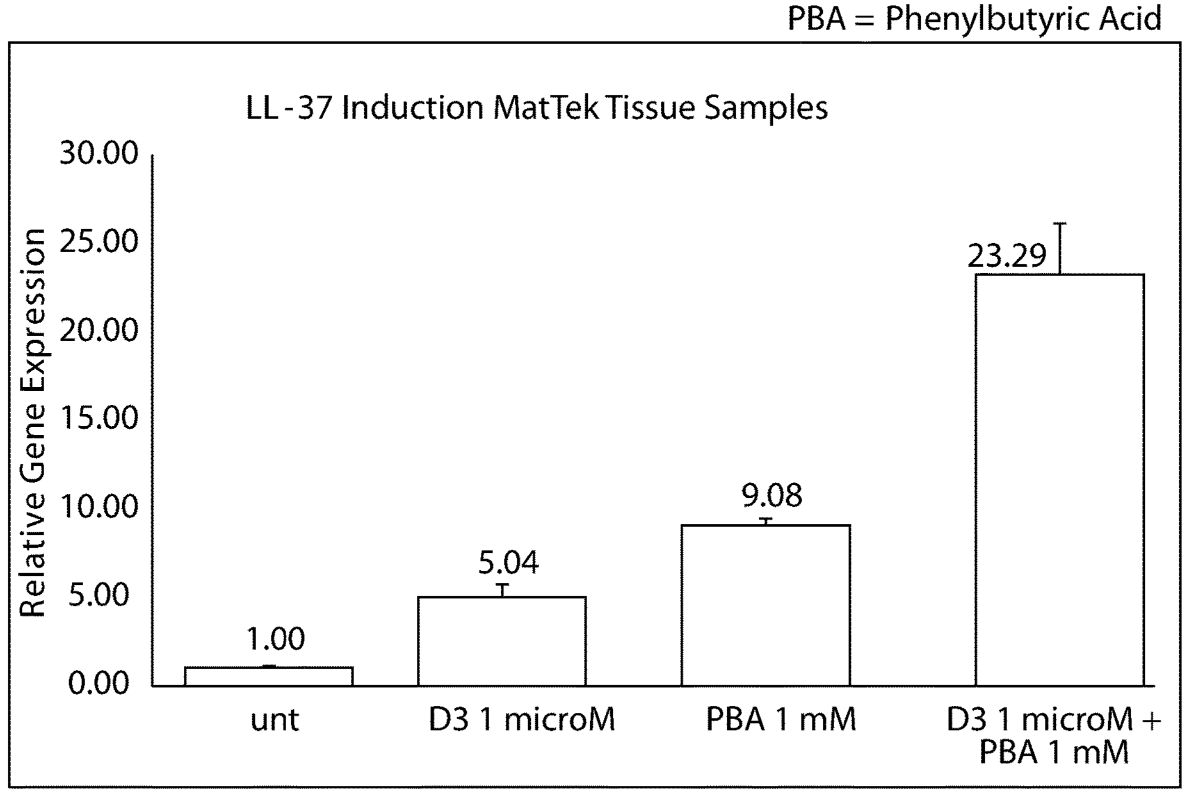

Gingival tissues (GIN 100) were purchased from Mattek Corporation. Tissues were treated in triplicate with Vitamin D3, Sodium Butyrate or Phenyl butyrate individually or in combination of two with indicated doses and tissues were incubated with these treatments overnight in tissue culture incubator. Tissues were collected and transferred in RNA later buffer and were frozen in −70° C. freezer. When ready for processing, tissues were homogenized and processed for RNA isolation and c-DNA preparation and qPCR amplification as described above using LL-37 and GAPDH specific Taqman probes. The results are described in FIGS. 3A and 3B. As illustrated by the data described in FIGS. 3A and 3B, the inventive combinations of the present invention provide a synergistic increase in LL-37.

While the present invention has been described with reference to several embodiments, which embodiments have been set forth in considerable detail for the purposes of making a complete disclosure of the invention, such embodiments are merely exemplary and are not intended to be limiting or represent an exhaustive enumeration of all aspects of the invention. The scope of the invention is to be determined from the claims appended hereto. Further, it will be apparent to those of skill in the art that numerous changes may be made in such details without departing from the spirit and the principles of the invention.

What is claimed is:

1. An oral care composition comprising:

vitamin D, or a derivative thereof;

an alkanoic acid of formula R—COOH or an alkali metal salt thereof, wherein R is a $C_1$ to $C_{13}$ hydrocarbyl group, wherein the vitamin D and/or the derivative thereof and the alkanoic acid and/or the alkali metal salt thereof is at a concentration of about 1 mM to about 4 mM; and an orally acceptable carrier, wherein the oral care composition is in the form of a toothpaste or a mouthwash.

2. The oral care composition according to claim 1, wherein R is R'—$(CH_2)_n$—, wherein n=1 to 3, and R' is H or a $C_1$ to $C_{12}$ hydrocarbyl group.

3. The oral care composition according to claim 1, wherein the vitamin D, or derivative thereof, is selected from: vitamin D1, ergocalciferol, lumisterol, vitamin D2, vitamin D3, cholecalciferol, vitamin D4, 22-dihydroergocalciferol, vitamin D5, sitocalciferol, calcitriol, vitamin D compounds with hydroxyl groups at 1, 3 and 25 carbon positions, esters of 1α,25-dihydroxy vitamin D3, esters of 1,25-dihydroxy vitamin D3, 1,25 $(OH)_2D3$ analogs of 1,25 $(OH)_2D3$, 25(OH)D3, analogs of 25(OH)D3 and mixtures thereof.

4. The oral care composition according to claim 1, wherein the vitamin D, or derivative thereof, is cholecalciferol.

5. The oral care composition according to claim 1, wherein an alkanoic acid of formula R—COOH or an alkali metal salt thereof, wherein R is a $C_1$ to $C_{13}$ hydrocarbyl group is selected from: sodium butyrate, phenylbutyrate, phenylbutyric acid; pyrenebutyric acid; and a combination of two or more thereof.

6. The oral care composition according to claim 1, wherein the vitamin D, or derivative thereof; and the alkanoic acid of formula R—COOH or an alkali metal salt thereof, wherein R is a $C_1$ to $C_{13}$ hydrocarbyl group, are present in an amount effective to provide an anti-inflammatory benefit.

7. The oral care composition according to claim 1, further comprising a metal ion source.

8. The oral care composition according to claim 7, wherein the metal ion source is selected from: a zinc ion source; a stannous ion source; a copper ion source; and a combination of two or more thereof.

9. The oral care composition according to claim 7, wherein the metal ion source is selected from: zinc oxide; zinc citrate; zinc phosphate; zinc pyrophosphate; zinc sulfate; stannous fluoride; stannous chloride; stannous gluconate; and a combination of two or more thereof.

10. The oral care composition according to claim 1, further comprising arginine.

11. A method of treating, preventing, or inhibiting an inflammatory disease, disorder or condition of the oral cavity comprising: administering an oral care composition according to claim 1 to a subject in need thereof.

12. The method according to claim 11, wherein the inflammatory disease, disorder or condition of the oral cavity is selected from gingivitis; periodontitis; ulcerative stomatitis; herpetic stomatitis; and oral herpes zoster.

13. A method of treating a bacterial infection of the oral cavity comprising administering an oral care composition according to claim 1, to an oral cavity surface of a subject in need thereof.

14. The oral care composition according claim 1, wherein the vitamin D and/or the derivative thereof is at a concentration of about 1 μM.

15. The oral care composition according claim 1, wherein the vitamin D and/or the derivative thereof is at a concentration of about 10 μM.

16. The oral care composition according claim 1, the vitamin D, or derivative thereof, is present in an amount of from about 0.001 wt. % to about 0.100 wt. %, based on the total weight of the oral care composition.

* * * * *